United States Patent [19]

Gaske et al.

[11] Patent Number: 4,649,045
[45] Date of Patent: Mar. 10, 1987

[54] COATING COMPOSITIONS AND NAIL POLISH COMPOSITIONS INCLUDING THE SAME

[75] Inventors: Joseph E. Gaske, Mt. Prospect; Edwin A. Zychowski, Des Plaines, both of Ill.

[73] Assignee: DeSoto, Inc., Des Plaines, Ill.

[21] Appl. No.: 847,504

[22] Filed: Apr. 3, 1986

[51] Int. Cl.$^4$ ..................... A61K 7/043; C08L 33/14
[52] U.S. Cl. ........................................ 424/61; 424/81; 524/46; 524/523; 525/223
[58] Field of Search ................ 524/522, 523; 525/223; 424/81, 61

[56] References Cited

U.S. PATENT DOCUMENTS 3,927,203 12/1975 Seymour ............................... 424/61
4,273,145 6/1981 Lester ................................... 424/61
4,409,203 10/1983 Gordon ................................. 424/61

Primary Examiner—C. Warren Ivy
Attorney, Agent, or Firm—Dressler, Goldsmith, Shore, Sutker & Milnamow, Ltd.

[57] ABSTRACT

The present invention relates to coating compositions that include an admixture or blend of at least two solution copolymers that provide combinations of properties which are not possessed by coating compositions that include only one of the copolymers. Each solution copolymer contains at least one aromatic monoethylenic monomer and at least one monoethylenic ester in amounts sufficient to provide a first solution copolymer having a glass transition temperature between about 40 and 70 degrees Centigrade and a second solution copolymer having a glass transition temperature between about −10 and +10 degrees Centigrade. Pigments can be readily wetted and dispersed in the copolymer blend to provide stable pigment concentrates that are useful in the preparation of coating compositions suitable for use on human fingernails.

26 Claims, No Drawings

COATING COMPOSITIONS AND NAIL POLISH COMPOSITIONS INCLUDING THE SAME

TECHNICAL FIELD

The present invention relates to coating compositions that include an admixture or blend of at least two solution copolymers that provide combinations of properties which are not possessed by coating compositions that include only one of the copolymers. Pigments can be readily wetted and dispersed in the copolymer blend to provide stable color concentrates that are useful in the preparation of coating compositions suitable for use on human fingernails.

BACKGROUND ART

High gloss and wearability are desirable characteristics of any coating composition that is prepared to cover fingernails and similar substrates. The highest possible gloss and maximum resistance to wear are essential for any commercially useful nail polish.

It has been conventional practice for many years to use nitrocellulose as the film forming agent in nail polish compositions. The use of nitrocellulose has numerous disadvantages, but these disadvantages have generally been overlooked because of its low cost. For example, nitrocellulose is an explosive material that requires special handling during manufacture and use. Moreover, pigmented nitrocellulose-containing compositions are not particularly stable in the presence of light and tend to yellow upon storage.

Certain copolymers have been added to nitrocellulose-containing compositions to reduce the amount of nitrocellulose used and to improve the appearance of the coated material. Although these copolymers may provide an adequate coating composition, the adhesion of the coating composition to the substrate and the gloss of the film was often less than desirable.

The poor wetting characteristics of such compositions adversely influence coating utility because the substrate to be coated, such as a fingernail, must be wetted to allow the coating to spread evenly. Poor wetting also contributes to poor adhesion and cracking of the film.

DISCLOSURE OF THE INVENTION

The present invention relates to solvent solution thermoplastic coating compositions that include an admixture or blend of at least two solution copolymers that provide combinations of properties which are not possessed by coating compositions that include only one of the copolymers. Pigments can be readily wetted and dispersed in the copolymer blend to provide stable color concentrates that are useful in the preparation of coating compositions suitable for use on human fingernails.

A coating composition according to one embodiment of the invention comprises an admixture of from about 40 percent to about 60 percent of a first solution copolymer and from about 60 percent to about 40 percent of a second solution copolymer. In this embodiment, the preferred proportion of the first solution copolymer to the second solution copolymer is 1:1.

All proportions and ratios including those in the accompanying Examples and claims are by weight unless otherwise specified.

Each solution copolymer comprises from about 40 percent to about 80 percent of an aromatic monoethylenic monomer together with a mixture of about 5 percent to about 40 percent of an aliphatic monoethylenic ester, at least about 0.5 percent to about 15 percent, preferably from 2 to 10 percent, of a hydroxy alkyl ester of a monoethylenic carboxylic acid to provide pigment wetting and adhesion and at least about 0.5 percent to about 8 percent, preferably from 2 to 7 percent, of a monoethylenic carboxylic acid for the same purpose. The latter two monomers also enable hydrogen bonding. The foregoing proportions are based on the total weight of the monomers copolymerized.

Selection of the appropriate monomers and their proportions of use provide a first solution copolymer with a glass transition temperature in the range of about 40 degrees Centigrade to about 70 degrees Centigrade and a second solution copolymer with a glass transition temperature in the range of about $-10$ degrees Centigrade to about $+10$ degrees Centigrade. The final glass transition temperature is calculated as a weighted average of all the monomers that are employed and their proportion of use.

It has been found that solvent solution thermoplastic coating compositions that include appropriate blends of the specified relatively high Tg copolymers and relatively low Tg copolymers produce non-tacky, solid films that are tougher, harder and more durable than films formed of coating compositions that include only a single copolymer containing all the monomers of both copolymers.

In a more preferred embodiment, the admixture comprises about 50 percent of the first solution copolymer and about 50 percent of the second solution copolymer so that the admixture is 1:1 by weight of the individual copolymers, the glass transition temperature of the first solution copolymer is from about 50 to 60 degrees Centigrade and the glass transition temperature of the second solution copolymer is from about $-5$ to $+5$ degrees Centigrade.

The aromatic monoethylenic monomer is preferably selected from styrene, vinyl toluene and alpha-methyl styrene. The use of styrene, however, is preferred.

Suitable monoethylenic esters include acrylic and methacrylic acid esters formed with an alkanol having from about 1 to about 18 carbon atoms, preferably from 4 to 10 carbon atoms. Such materials include ethyl acrylate, n-butyl acrylate, isobutyl acrylate, 2-ethyl hexyl acrylate, decyl acrylate, dodecyl acrylate and the corresponding methacrylates. The use of 2-ethyl hexyl acrylate is particularly preferred in the copolymer having the lower glass transition temperature.

The inclusion of appropriate monoethylenic esters in the aromatic monoethylenic monomer-containing copolymer and the selection of appropriate monomer proportions lowers the glass transition temperature of the copolymer. The selection and proportion of monomers to obtain a copolymer having any desired glass transition temperature is itself well known in polymer chemistry.

The copolymers which are blended together in this invention include at least about 0.5 percent of an appropriate hydroxy alkyl ester of a monoethylenically unsaturated carboxylic acid including 2-hydroxy ethyl acrylate, 2-hydroxy propyl acrylate, 2-hydroxy butyl acrylate and the corresponding methacrylates to provide compatability with water. The proportion of such hydroxy alkyl ester is less than about 15 percent, and more preferably between 2 percent and 10 percent, based on the total weight of the monomers copolymerized. In addition, the inclusion of at least about 0.5 percent of a monoethylenically unsaturated carboxylic acid including acrylic acid and methacrylic acid provides adhesion to the substrate. The proportion of monoethylenic carboxylic acid is preferably less than about 8 percent, and more preferably between 2 percent and 7 percent, based on the total weight of the monomers copolymerized. The use of 2-hydroxy ethyl acrylate and acrylic acid is preferred.

It is also possible to use a larger than desired proportion of the monoethylenic carboxylic acid and then post-react the preformed copolymer with a monoepoxide like ethylene oxide, propylene oxide or butylene oxide to thus reduce the acid content into the desired range by, in essence, forming the hydroxy monomer in situ.

The copolymers of this invention are prepared by free radical polymerization in organic solvent solution. For purposes of illustration, styrene (an aromatic monoethylenic monomer) and 2-ethyl hexyl acrylate (a monomer that is an aliphatic monoethylenic ester) are two monomers used to prepare copolymers in the following Examples. Variation in the ratio of styrene to 2-ethyl hexyl acrylate permits preparation of copolymers having varying physical properties. For example, a copolymer prepared with a high proportion of styrene provides a hard, brittle film and has a relatively high glass transition temperature (Tg). A copolymer prepared with a high proportion of 2-ethyl hexyl acrylate provides a soft, flexible film and has a relatively low Tg. Of course, different esters can be used in the different copolymers.

These copolymers form films, upon application to a substrate followed by evaporation of the solvent, which have predictable characteristics based on the theoretical Tg values. Such polymeric solutions can be used to wet and disperse pigments that are known to be safe for contact with human skin. Moreover, pigment concentrates can be prepared using conventional dispersing equipment, such as sand mills. Pigment grinding involves no hazard as is usually encountered using nitrocellulose. The pigment concentrates of this invention are color-stable and resist yellowing.

Such pigment concentrates, which are also referred to herein as "pigmented solvent solution concentrates", are provided with a relatively high non-volatile solids content, preferably in the form of a homogeneous gel. The pigment concentrate can, of course, also be formed as a slurry by increasing the amount of solvent in the concentrate.

The pigment concentrates of this invention include at least about 20 percent, based on the total weight of the concentrate, of a pigment dispersed in a nail polish-acceptable volatile organic solvent, a thickening agent in an amount sufficient, preferably less than 2 percent by weight, to increase the viscosity of the concentrate to the desired level, water in an amount sufficient, preferably less than 2 percent by weight, to allow the thickening agent to be effective and a blend of solution copolymers as described herein.

Suitable organic pigments include metallic resinate lakes of D&C Red Nos. 6, 7, 10, 11, 12 and 13; D&C Red No. 34; and D&C Yellow No. 5. It is also possible to use inorganic pigments such as titanium dioxide, bismuth oxychloride, brown iron oxide, black iron oxide, red iron oxide and chrome oxide. Ultramarine blue, ultramarine rose, ultramarine violet, mango violet, phthalocyanine blue and the like may also be used.

The nail polish-acceptable volatile organic solvent is preferably selected from ester solvents including n-butyl acetate, ethyl acetate and n-propyl acetate used alone or in admixture with an aromatic solvent such as toluene, a ketone solvent such as methyl ethyl ketone or an alcohol solvent such as isopropyl alcohol.

Suitable thickening agents are quaternized amine-modified clays which include quaternized montmorillonite-type clays (such as stearyl alconium hectorites), hectorites, quaternized amine-modified kaolin clays and the like. The thickening agent stably suspends the pigment when the pigment concentrate is diluted with the volatile organic solvent to a level appropriate for use in a nail polish composition, typically 20 to 50 percent by weight.

Water is added alone or together with other agents, such as orthophosphoric acid, that render the thickening agent more effective in suspending the pigment. The amount of water added is as little as possible, preferably just enough to allow the thickening agent to function. The proportions of the thickening agent and water may be appropriate to form a gel. The formation of a gel is preferable, but not essential.

It is also desirable, but not essential, to add to the pigment concentrate from about 2 percent to about 10 percent, preferably from 3 to 8 percent, of ethyl cellulose based on the total weight of the concentrate. Another desirable, but not essential, component which may be added in the same proportions noted above are ester plasticizers including dioctyl adipate, dioctyl phthalate, dibutyl phthalate and tricresyl phosphate.

These pigment concentrates are similar in consistency to color concentrates used by artists and remain stable with no flocculation, separation or settling after storage for prolonged periods of time. The color bases can be conveniently blended. Polymer solutions together with additives, such as anti-settling agents, plasticizers, surfactants and the like may be incorporated by blending to produce glossy, very adherent, fingernail coatings having the ability to almost completely hide the underlying nail surface with a single coat. Air-dried coating films are soluble in commercial fingernail polish remover which includes a mixture of acetone and water.

A series of such copolymers with varying Tg values was prepared. As mentioned above, it was found that coating compositions comprising blends of high and low Tg copolymers produced dry, solid films that were tougher, harder and more durable than films formed of coating compositions that included only one of the copolymers. This result was completely unexpected. Although the present invention is not to be limited to theory, it is thought that the association of the two related copolymers, perhaps by hydrogen bonding and other inter-micellar crystallization, produces associated structures of hard and rigid linear chain members and soft and flexible linear chain members that provide the desired solid plastic coatings which are harder, tougher and more durable than a single copolymer of the same Tg as the blends produced herein.

Further studies demonstrated that such copolymer blends may be prepared using "tailor made" copolymers to provide greater latitude in the formulation of tough, durable and resilient coating compositions by blending solutions of appropriate copolymers. The use of such techniques in the production of fingernail coating compositions simplifies manufacture and provides a versatile process in that the total solids content of the composition can be increased and the ability of such coating compositions to hide the underlying nail surface can be enhanced without sacrificing other desirable properties.

Moreover, the copolymers of this invention are safer to handle than nitrocellulose-based polymers, which are now commonly used in the industry, because the copolymers are not as combustible, are non-explosive and are not degraded by exposure to light during storage. In addition, rheological properties can be more easily adjusted to accommodate a wider range of application methods.

A typical solution polymerization reaction is used to prepare the copolymers of this invention. A four-necked glass flask is equipped with a stirrer, a water-cooled condenser, a nitrogen inlet to exclude atmospheric oxygen, a thermometer, means for heating and cooling the flask and dropping funnels for separately introducing an appropriate monomer mixture and an initiator solution into the reaction flask. The flask is charged with 80 parts by weight of n-butyl acetate.

An initiator solution may be prepared by mixing 20 parts butyl acetate, 0.5 parts odorless mineral spirits, 0.5 parts t-butyl peroctoate, 0.5 parts t-butyl perbenzoate and 0.5 parts di-t-butyl peroxide. Other suitable initiator solutions are well known to those skilled in the art of free radical polymerization.

The reaction flask containing the n-butyl acetate is blanketed with nitrogen and is heated to 100 degrees Centigrade. At 100 degrees C., 100 parts of a monomer mixture (such as those monomer mixtures listed herein with reference to copolymers A-E of Example 1 which follows) and 22 parts of the foregoing initiator solution are simultaneously, but separately, added dropwise to the flask. The monomer mixture is added over a four hour period, and the initiator solution is added over a period of about four and one-quarter hours. The temperature is maintained at about 100 degrees C. during the additions, with very little or no refluxing. Intermittent cooling may be necessary to maintain the desired temperature. After the additions are completed, the temperature is raised to the reflux temperature (125-130 degrees C.), and the reaction mixture is maintained at that temperature until conversion is complete (2-4 hours).

Copolymers A-E, as shown in the following Table of Example 1, were prepared using the foregoing polymerization technique. The n-butyl acetate used was anhydrous ("urethane grade") solvent. Anhydrous solvents were used in all the Examples.

EXAMPLE 1

| Copolymer* | A | B | C | D | E |
|---|---|---|---|---|---|
| Styrene | 72.5 | 48.5 | 75.4 | 60.6 | 60.5 |
| Butyl acrylate | — | — | — | — | — |
| 2-Ethylhexyl acrylate | 7.5 | 31.5 | 4.6 | 18.4 | 19.5 |
| 2-Hydroxyethyl acrylate | 5.0 | 5.0 | 5.0 | 5.0 | 5.0 |
| Acrylic acid | 5.0 | 5.0 | 5.0 | 5.0 | 5.0 |
| Tg, °C. (Theoretical) | 55 | 0 | 63 | 27.5 | 25 |
| Non-Volatile materials (percent) | 49.8 | 49.3 | 49.7 | 48.7 | 48.3 |
| Viscosity (cps) | 1880 | 1140 | 2000 | 1500 | 1600 |
| Wt./Gal. (lbs) | 8.21 | 8.13 | 8.22 | 8.16 | 8.16 |

*The listed proportions of each monomer are by weight.

As previously mentioned, a coating composition that includes a single copolymer (such as copolymer D or E) does not perform as well as a nail polish composition as those compositions that include a blend of relatively high and low Tg copolymers.

The coating compositions of this invention are normally applied in any desired fashion to provide a film having a thickness adequate to provide a dry film that is from about 0.25 to 4 mils thick, but preferably from 1 to 2 mils thick. The wet film is allowed to thicken by vaporization of the volatile constituents which is usually carried out at room temperature over a period of from 5 to 10 minutes.

Wet films having thicknesses of about 5 mils (which correspond to dry film thicknesses of about 2 mils) were applied to glass plates using standard application procedures. Specifically, a blend of the copolymers A and B (1:1 by weight) was used to prepare one set of films. These individual copolymers have Tg values of 55 degrees C. and 0 degrees C., respectively. It is reasonable to assume that such a 1:1 blend would demonstrate a Tg value that is approximately equal to the numerical average of the two individual copolymers, e.g. about 27.5 degrees C.

Copolymer D was specifically formulated to have a Tg of about 27.5 degrees C., and was therefore applied in a similar manner to glass plates to form a second series of films. The same ratio of total monomers that was present in the 1:1 blend of the copolymers A and B was used to prepare an additional copolymer (copolymer E), which was also used to form films on glass plates.

The films were tested for hardness after being thoroughly air dried at room temperature and warmed in an air oven as specified by Gardner test method 5.1.3.4, which is commonly referred to as the "Sward Rocker" test. The Sward Rocker test measures the hardness of organic coating films within the elastic limits of the resin. The tests were performed at 24 degrees C. and at 33 percent relative humidity with the rocker standardized to 50 (plus or minus one) rock/minute on a clean uncoated glass plate. This was selected as the 100 percent value.

The results of the Sward Rocker test of these three films are shown below.

| | Sward Rocker Hardness |
|---|---|
| Admixture of copolymers A and B (1:1 by weight) | 84(+2,−4) percent |
| Copolymer E | 72(+2,−2) percent |
| Copolymer D | 80(+4,−2) percent |

As shown in the data tabulated above, the 1:1 copolymer blend was harder than a single copolymer made using an identical composition of monomers as the average monomer composition in the blend (copolymer E). The film of copolymer D had the same Tg value that one would expect of the blend and had about the same hardness. Upon scratching these films with a hand-held knife, it was observed that the film formed of the 1:1 copolymer blend was the toughest and most resilient of the three films. A ribbon of the film formed of the 1:1 copolymer blend was removed upon scratching the film surface with a hand-held knife, while the films formed of copolymers D and E shattered and were brittle.

Admixtures of copolymers B and C also yielded hard, tough films, but copolymer C (because of its higher styrene content) increased in viscosity very rapidly with even a slight increase in non-volatile solids content. This was the result of solvent evaporation upon brush application and produced a "cobweb-like" stringing of the material as the brush was removed from the fingernail. Coincidentally, this same property was observed using a solution of a polyethyl methacrylate (such as the material sold by DuPont under the trade name "Elvacite 2042") which has the same Tg value as copolymer C.

The 1:1 copolymer blend is preferred for use as a fingernail coating composition. Blends of less than or more than about 40 percent:60 percent (by weight) were either too soft and tacky or too hard, brittle and inflexible such that the film shattered when scratched during the knife adhesion test.

EXAMPLE 2—FINGERNAIL COATING COMPOSITION 20.2 Grams of n-butyl acetate, 5.0 grams of ethyl acetate, 20.0 grams of slurry of thickening agent and 1.0 gram of a one percent (by weight) solution of non-functional Nylon P1155 (Krumbhaar Resin Div., Lawter Chemicals, Moundville, Ala.) in n-propanol were mixed thoroughly while 25.0 grams of copolymer A and 23.7 grams of copolymer B were slowly added. The mixture was stirred until homogeneous.

The slurry of thickening agent was prepared by thoroughly mixing 240 grams of n-butyl acetate and 30 grams of Hectorite (Bentone SD-2 supplied by National Lead Co., RD Number:9777022-31-3) using a high shear agitator until the hectorite was thoroughly wetted. With continuous high speed, high shear mixing 22.5 grams of deionized water was slowly added. Mixing was continued until a smooth uniform gel was formed. Then 90 grams of copolymer A and 90 grams of copolymer B (both from Example 1) were slowly added. Thereafter, 120 grams of n-butyl acetate were added slowly with stirring.

The following pigment concentrates were combined and added to the foregoing mixture: 7.0 grams of a D&C Red No. 6 pigment concentrate, 1.2 grams of a D&C Red No. 7 pigment concentrate and 1.6 grams of a titanium dioxide pigment concentrate.

The D&C Red No. 6 pigment concentrate was prepared by combining 820 grams of D&C Red No. 6, Barium Lake (RD Number: 977058-86-8) and 1100 grams of anhydrous n-butyl acetate with stirring to thoroughly wet the dry pigment. To the mixture was added with stirring 800 grams of copolymer B. The resulting mixture was formed into a smooth uniform paste and 20 grams of Hectorite was slowly added with stirring. The composition was fixed in a Cowles mixer to a smooth lump free consistency and was ground in a sand mill to a Nortn Standard fineness of about 7½+. To this dispersed paste was added with mixing 160 grams of copolymer B and 340 grams of n-butyl acetate to provide a composition having a total weight of about 3240 grams.

Percent Composition (by weight)
  0.61 percent Hectorite
  25.31 percent D&C Red No. 6, Barium Lake
  14.81 percent non-volatile resin (copolymer B)
  59.27 percent volatile solvent (n-butyl acetate)

The D&C Red No. 7 pigment concentrate was prepared by dispersing D&C Red No. 7, Calcium Lake (RD Number:977054-36-6) in a manner similar to that described above. The final composition was:

Percent Composition (by weight)
  0.2 percent Hectorite
  20.2 percent D&C Red No. 7, Calcium Lake
  12.3 percent non-volatile resin (copolymer B)
  67.3 percent volatile solvent (n-butyl acetate)

The titanium dioxide pigment concentrate was prepared by dispersing titanium dioxide (CAS Number:13463-67-7) in a manner similar. The final composition was:

Percent Composition (by weight)
  0.2 percent Hectorite
  44.2 percent titanium dioxide
  22.5 percent non-volatile resin (copolymer B)
  33.1 percent volatile solvent (n-butyl acetate)

Thereafter, 1.2 grams of a 10 percent (by weight) solution of Union Carbide "Silwet L-7001" (a dimethicone copolymer) in anhydrous n-butyl acetate was added to the composition.

The composition of Example 2 was coated onto a glass plate using a 4 mil Bird applicator. Several commercial nitrocellulose-based nail polishes, selected as having a color very similar to that of the composition of Example 2, were applied in the same manner. Each material was air dried at room temperature for 3 days followed by storage in a hot air laboratory oven chamber for 4 hours.

The opacity of the film of Example 2 was much greater than the opacities of the commercial nitrocellulose-based samples, and instrumentally measured gloss, at an incidence angle of 60 degrees, was 100 gloss units. This was higher than the commercial films by about 5 gloss units (on the average).

A sample of the composition of Example 2 was stored in a closed container at 55 degrees C. for a period of 100 hours, cooled to room temperature, and the viscosity was measured an additional time to test storage stability. There was no viscosity change as measured by the Brookfield viscometer using the complete low to high shear rate capability of the instrument to quantify the obvious thixotropy; i.e. viscosity was highest at very low shear rates and a typical "hysteresis loop" was observed on graphically plotting viscosity as a function of shear rate (revolutions per minute), starting at the lowest shear rate, proceeding step-wise to the highest shear rate, and then returning to the lowest (initial) shear rate in uniformly timed short intervals.

A clear glass vial was filled two-thirds with the composition of Example 2, sealed and exposed to sunlight for a period of 30 days at room temperature. No pigment settling or separation at the air interface occurred during that period. Films applied onto glass plates were unchanged in color compared to those stored in opaque containers. It is known, however, that some of the pigments that are used to produce such fingernail coatings are not particularly stable in the presence of light. Light stabilizers may be added to the coating composition to retard color change in such cases as is well known to those skilled in the art.

Tests on human fingernails were performed by a group of women who routinely use fingernail polish and who are familiar with the properties of such polishes. In all cases the ease of application, air drying, gloss, appearance, resistance to chipping, wear and general durability characteristics were reported as being better than those of commercial nitrocellulose-based products.

The daily activities of one woman included six hours per weekday as a typist along with dishwashing, housework and other normal activities of a working wife and mother. The coating composition of Example 2 outlasted commercial polishes she had previously used and remained intact and attractive for a full week. Currently available commercial polishes have an average durability of only about 4 days under the same conditions of use.

The composition of Example 2 can be modified in various ways by the addition of other components and additives. For example, camphor may be used to aid in solvating some non-functional reinforcing Nylons by using this material in combination with an alcohol and water. Camphor aids in achieving rheological properties that prevent the settling of denser pigments such as titanium dioxide, iron oxides and titanated mica particles when used in conjuction with Hectorite and Nylon.

It is understood that for obvious reasons the presence of formaldehyde in nail polishes should be avoided. The polymers and compositions of this invention exhibit moisture vapor and oxygen transmission rates higher than, or at least equal to, commercial nail polishes. This is a very desirable property in avoiding the growth of microflora on the human fingernail. It is not known that the commonly used toluenesulfonamide/formaldehyde resin (CAS Number:PM9008-60-0) acts in this capacity, certainly it is well known that formaldehyde is an excellent bacteriostatic agent and fungicide. Such formaldehyde resins can be used in the present compositions as plasticizers, and have been found to be useful as coupling agents, enabling the incorporation of other, rather incompatible, materials.

Amino-functional Nylon-type modifiers, such as the Versamid resins of Henkel Corp. are excellent modifiers that initially yield highly desirable rheological properties. Upon storage at 55 degrees C. for about 100 hours, or at room temperature for prolonged periods, however, this initial thixotropy is lost. Non-amino functional Nylons are preferred since they are essentially neutral, having no amino alkalinity to (apparently) hydrolyze the acrylic portions of the copolymers. The amino groups can be deactivated by Michael reaction with acrylate monomers added in stoichiometric amounts. This has been found to render such materials more compatible with the present copolymers providing effective plasticizers which upon quaternization with, for example, hydrochloric acid provide effective bacteriostatic agents and fungicides.

It is also desirable to avoid the presence of residual styrene in the coating composition. Any amounts of unreacted styrene in the solution copolymer can be reacted with a monomer other than styrene such as an unsaturated anhydride including maleic anhydride or a half ester thereof.

The present copolymers, which are polar and which include hydrophobic and hydrophyllic groups on the same polymeric chain, readily wet organic and inorganic pigments. As a result of these properties, the copolymers aid in the formation of stable colloidal systems which are required to prepare concentrated pigment dispersions. Pigments can be dispersed directly in the copolymer solutions utilizing efficient high speed mills. This provides uniformity and color control in the formation of these pigment concentrates.

Moreover, the present copolymers (unlike nitrocellulose) do not constitute a fire hazard, and no special precautions need be taken when handling the copolymers except that the flash point of the particular solvents used requires careful handling. But such precautions are commonplace in solvent-based paint and coating operations and workers in that industry are familiar with the necessary safety procedures.

The light stability of compositions containing present copolymers is superior to that of nitrocellulose. This improves the long term storage stability of the compositions. Such stability is a considerable problem with nitrocellulose-based nail polish compositions. This enhances the marketability of the present composition and decreases the costs associated with spoilage.

What is claimed is:

1. A solvent solution thermoplastic coating composition comprising an admixture of from about 40 percent to about 60 percent of a first solution copolymer and from about 60 percent to about 40 percent of a second solution copolymer, based on the total weight of the mixture of copolymers, said solution copolymers each comprising from about 40 percent to about 80 percent of an aromatic monoethylenic monomer together with a mixture of about 5 percent to about 40 percent of a monoethylenic ester formed with an alkanol having from about 1 to about 18 carbon atoms, from about 0.5 percent to about 15 percent of a hydroxy alkyl ester of a monoethylenic carboxylic acid and from about 0.5 percent to about 8 percent of a monoethylenic carboxylic acid, said proportions being based by weight on the total weight of monomers copolymerized to form each of the respective copolymers, to provide the first solution copolymer with a glass transition temperature in the range of about 40 degrees Centigrade to about 70 degrees Centigrade and the second solution copolymer with a glass transition temperature in the range of about −10 degrees Centigrade to about +10 degrees Centigrade.

2. The coating composition according to claim 1 wherein said hydroxy alkyl ester of said monoethylenic carboxylic acid comprises from about 2 percent to about 10 percent of the total weight of the monomers copolymerized.

3. The coating composition according to claim 1 wherein said monoethylenic carboxylic acid comprises from about 2 percent to about 7 percent of the total weight of the monomers copolymerized.

4. The coating composition according to claim 1 wherein said admixture comprises 50 percent of the first solution copolymer and 50 percent of the second solution copolymer.

5. The coating composition according to claim 1 wherein said first solution copolymer has a glass transition temperature in the range of 50 degrees Centigrade to 60 degrees Centigrade.

6. The coating composition according to claim 1 wherein said second solution compolymer has a glass transition temperature in the range of −5 degrees Centigrade to +5 degrees Centigrade.

7. The coating composition according to claim 1 wherein said aromatic monoethylenic monomer is selected from the group consisting of styrene, vinyl toluene and alpha-methyl styrene.

8. The coating composition according to claim 1 wherein said aromatic monoethylenic monomer is styrene.

9. The coating composition according to claim 1 wherein said monoethylenic ester is an acrylic or methacrylic acid ester formed with an alkanol having from 1 to 18 carbon atoms.

10. The coating composition according to claim 1 wherein said monoethylenic ester is an acrylic or methacrylic acid ester formed with an alkanol having from 4 to 10 carbon atoms.

11. The coating composition according to claim 1 wherein said monoethylenic ester is selected from the group consisting of ethyl acrylate, n-butyl acrylate, isobutyl acrylate, 2-ethyl hexyl acrylate, decyl acrylate, dodecyl acrylate and the corresponding methacrylates.

12. The coating composition according to claim 1 wherein said monoethylenic ester is 2-ethyl hexyl acrylate.

13. The coating composition according to claim 1 wherein said hydroxy alkyl ester of said monoethylenic carboxylic acid is selected from the group consisting of 2-hydroxyethyl acrylate, 2-hydroxypropyl acrylate, 2-hydroxybutyl acrylate and the corresponding methacrylates.

14. The coating composition according to claim 1 wherein said hydroxyalkyl ester of said monoethylenic carboxylic acid is 2-hydroxyethyl acrylate.

15. The coating composition according to claim 1 wherein said monoethylenic carboxylic acid is selected from the group consisting of acrylic acid and methacrylic acid.

16. The coating composition according to claim 1 wherein said monoethylenic carboxylic acid is acrylic acid.

17. The coating composition according to claim 1 wherein said composition includes a pigment.

18. A coating composition comprising an admixture of from about 40 percent to about 60 percent of a first solution copolymer and from about 60 percent to about 40 percent of a second solution copolymer, based on the total weight of the mixture of copolymers, said solution copolymers each comprising from about 40 percent to about 80 percent styrene together with a mixture of about 5 percent to about 40 percent of 2-ethyl hexyl acrylate, from about 0.5 percent to about 15 percent of 2-hydroxy ethyl acrylate, and from about 0.5 percent to about 8 percent of acrylic acid, said proportions being based by weight on the total weight of monomers copolymerized to form each of the respective copolymers, to provide the first solution copolymer with a glass transition temperature in the range of about 40 degrees Centigrade to about 70 degrees Centgrade and the second solution copolymer with a glass transition temperature in the range of about −10 degrees Centigrade to about +10 degrees Centigrade.

19. A pigmented solvent solution concentrate comprising at least about 20 percent of a pigment dispersed in a nail polish-acceptable volatile organic solvent containing an amount of a thickening agent sufficient to stably disperse the pigment, water in an amount sufficient to enable the thickening agent to stably disperse the pigment and from about 10 percent to about 30 percent of the coating composition of claim 1, said proportions being based by weight on the total weight of the concentrate.

20. The pigmented concentrate of claim 19 including from about 2 percent to about 10 percent of ethyl cellulose.

21. The pigmented concentrate of claim 19 including from about 2 percent to about 10 percent of an ester plasticizer.

22. A pigmented solvent solution concentrate comprising at least about 20 percent of a pigment dispersed in a nail polish-acceptable volatile organic solvent containing an amount of a thickening agent sufficient to stably disperse the pigment, water in an amount sufficient to enable the thickening agent to stably disperse the pigment and from about 10 percent to about 30 percent of the coating composition of claim 18, said proportions being based by weight on the total weight of the concentrate.

23. A nail polish composition including the coating composition of claim 1.

24. A nail polish composition including the coating composition of claim 18.

25. A nail polish composition including the pigmented solvent solution concentrate of claim 19.

26. A nail polish composition including the pigmented solvent solution concentrate of claim 22.

* * * * *